US008380278B2

(12) United States Patent
Maeda et al.

(10) Patent No.: US 8,380,278 B2
(45) Date of Patent: Feb. 19, 2013

(54) IMAGE CAPTURING APPARATUS, IMAGE CAPTURING METHOD, AND COMPUTER READABLE MEDIUM

(75) Inventors: Kiyohiro Maeda, Ashigarakami-gun (JP); Azuchi Endo, Ashigarakami-gun (JP); Hiroshi Yamaguchi, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 371 days.

(21) Appl. No.: 12/684,532

(22) Filed: Jan. 8, 2010

(65) Prior Publication Data

US 2010/0179437 A1 Jul. 15, 2010

(30) Foreign Application Priority Data

Jan. 14, 2009 (JP) ................................. 2009-005821

(51) Int. Cl.
*A61B 5/00* (2006.01)
(52) U.S. Cl. ......... 600/407; 600/160; 600/302; 600/477
(58) Field of Classification Search .................. 600/302, 600/407, 473, 475–479, 160
See application file for complete search history.

(56) References Cited

U.S. PATENT DOCUMENTS 5,590,660 A * 1/1997 MacAulay et al. ........... 600/478

FOREIGN PATENT DOCUMENTS

| JP | 3-118042 A | 5/1991 |
| JP | 5-203485 A | 8/1993 |
| JP | 2005-87728 | 4/2005 |

OTHER PUBLICATIONS

Notice of Reasons for Refusal dated Dec. 11, 2012 with English translation.

* cited by examiner

*Primary Examiner* — Ruth S Smith
(74) *Attorney, Agent, or Firm* — McGinn IP Law Group, PLLC

(57) ABSTRACT

Provided is an image capturing apparatus for generating a multi-band image for examining a disease condition which has little amount of information. The image capturing apparatus includes: a variable spectroscopic element capable of varying a wavelength of light to be transmitted; a wavelength band table recording therein wavelength bands corresponded with disease conditions; an observation target identifying section that identifies a disease condition to be observed; a variable spectroscopic element control section that controls the variable spectroscopic element to sequentially transmit light rays of a plurality of wavelengths within a range of a wavelength band recorded in the wavelength band table in correspondence with the disease condition identified by the observation target identifying section; and an image capturing section that sequentially captures images by means of the light rays of a plurality of wavelengths transmitted through the variable spectroscopic element.

19 Claims, 6 Drawing Sheets

IMAGE CAPTURING APPARATUS, IMAGE CAPTURING METHOD, AND COMPUTER READABLE MEDIUM

CROSS REFERENCE TO RELATED APPLICATION

The present application claims priority from a Japanese Patent Application No. 2009-005821 filed on Jan. 14, 2009, the contents of which are incorporated herein by reference.

BACKGROUND

1. Technical Field

The present invention relates to an image capturing apparatus, an image capturing method, and a computer readable medium for capturing the image of each of light rays of a plurality of wavelengths.

2. Description of the Related Art

Japanese Patent Application Publication No. 2005-87728 (Patent Document No. 1) discloses a technique for detecting a cancer by detecting light rays of a plurality of wavelengths in the wavelength band of 600-2000 nm using a photoelectric converter and transmitting the detected information to outside of an encapsulated endoscope via an antenna.

However, Patent Document No. 1 can only detect a cancer. If a plurality of types of disease conditions are to be detected, the photoelectric converter has to detect a signal for each wavelength across a wide wavelength band, which increases the amount of information.

SUMMARY

According to a first aspect of the innovations herein, provided is an image capturing apparatus including: a variable spectroscopic element capable of varying a wavelength of light to be transmitted; a wavelength band table recording therein wavelength bands corresponded with disease conditions; an observation target identifying section that identifies a disease condition to be observed; a variable spectroscopic element control section that controls the variable spectroscopic element to sequentially transmit light rays of a plurality of wavelengths within a range of a wavelength band recorded in the wavelength band table in correspondence with the disease condition identified by the observation target identifying section; and an image capturing section that sequentially captures images by means of the light rays of a plurality of wavelengths transmitted through the variable spectroscopic element.

The variable spectroscopic element control section controls the variable spectroscopic element to transmit light of a wavelength within the range of the wavelength band corresponding to the disease condition identified by the observation target identifying section, at a wavelength interval shorter than a wavelength interval of light of a wavelength outside the wavelength band corresponding to the identified disease condition.

The variable spectroscopic element control section controls the variable spectroscopic element to transmit, at a predetermined wavelength interval, light of a wavelength within a wavelength band range including the wavelength bands respectively corresponding to the disease conditions recorded in the wavelength band table, and when the observation target identifying section has identified a disease condition, the variable spectroscopic element control section controls the variable spectroscopic element to transmit light of a wavelength band corresponding to the identified disease condition, at a wavelength interval shorter than the predetermined wavelength interval.

According to a width of the wavelength band corresponding to the disease condition identified by the observation target identifying section, the variable spectroscopic element control section varies a wavelength interval of light transmitted within the range of the wavelength band corresponding to the identified disease condition.

The image capturing apparatus may further include a multi-band image generating section that generates a multi-band image indicating, for each of a plurality of pixels of the image capturing section, intensity of the light rays of a plurality of wavelengths sequentially captured by the image capturing section, where the observation target identifying section identifies the disease condition to be observed, by analyzing the multi-band image.

According to a second aspect of the innovations herein, provided is an image capturing method including: identifying a disease condition to be observed; obtaining a wavelength band corresponding to the identified disease condition, from a wavelength band table recording therein wavelength bands corresponded with disease conditions; sequentially transmitting light rays of a plurality of wavelengths within a range of the obtained wavelength band, by controlling a variable spectroscopic element capable of varying a wavelength of light to be transmitted; and sequentially capturing images by means of the light rays of a plurality of wavelengths transmitted through the variable spectroscopic element.

According to a third aspect of the innovations herein, provided is a computer readable medium storing therein a program, the computer including a wavelength band table recording therein wavelength bands corresponded with disease conditions, the program causing the computer to function as: an observation target identifying section that identifies a disease condition to be observed; a variable spectroscopic element control section that controls a variable spectroscopic element to sequentially transmit light rays of a plurality of wavelengths within a range of a wavelength band recorded in the wavelength band table in correspondence with the disease condition identified by the observation target identifying section, the variable spectroscopic element capable of varying a wavelength of light to be transmitted; and an image capturing section that sequentially captures images by means of the light rays of a plurality of wavelengths transmitted through the variable spectroscopic element.

The summary of the invention does not necessarily describe all necessary features of the present invention. The present invention may also be a sub-combination of the features described above.

DESCRIPTION OF EXEMPLARY EMBODIMENTS

The invention will now be described based on the preferred embodiments, which do not intend to limit the scope of the present invention, but exemplify the invention. All of the features and the combinations thereof described in the embodiment are not necessarily essential to the invention.

Figure 1:
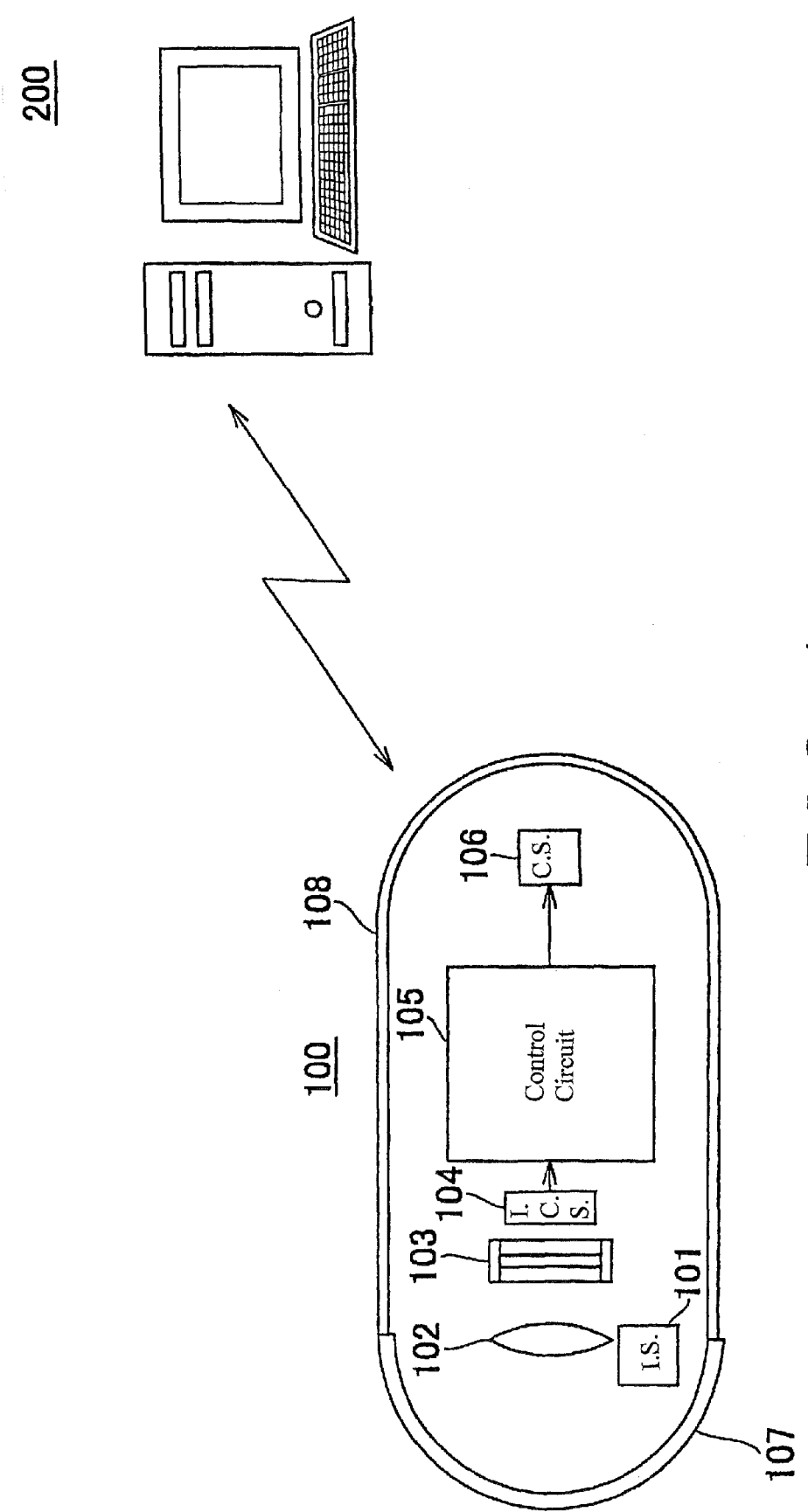
FIG. 1 shows an image capturing system according to an embodiment.

FIG. 1 shows an image capturing system according to an embodiment. The image capturing system includes an image capturing apparatus 100 and a computer 200. In the present embodiment, an encapsulated endoscope is taken as an example of the image capturing apparatus 100. The image capturing apparatus 100 includes an irradiating section (I.S.) 101, a lens 102, a variable spectroscopic element 103, an image capturing section (I.C.S.) 104, a control circuit 105, a communicating section (C.S.) 106, a transparent cover 107, and a case 108. An examinee swallows the image capturing apparatus 100 so that the image capturing apparatus 100 capture the image of the living tissue such as esophagus, stomach, and intestine of the examinee.

The irradiating section 101, the lens 102, the variable spectroscopic element 103, the image capturing section 104, the control circuit 105, and the communicating section 106 are provided in a housing including the transparent cover 107 and the case 108. The irradiating section 101 emits light to the subject being the living tissue. The irradiating section 101 includes a light source that emits light. The light source may be a light emitting element. The light emitted from the irradiating section 101 irradiates the subject after transmitted through the transparent cover 107. The irradiating section 101 may emit white light. The irradiating section 101 may emit light of a particular wavelength band. The irradiating section 101 may irradiate excitation light to excite fluorescent light. The light from the subject in response to the light emitted from the irradiating section 101 is incident to the lens 102 after transmitted through the transparent cover 107. The lens 102 focuses the light from the subject. The variable spectroscopic element 103 transmits light of a certain wavelength from the light having been transmitted through the lens 102. The variable spectroscopic element 103 is able to vary the wavelength of light to be transmitted. The variable spectroscopic element 103 may be an etalon for example. The image capturing section 104 captures an image of light of the wavelength having been transmitted through the variable spectroscopic element 103. The image capturing section 104 may include an image capturing element, an image capturing element driver, an AD converter, and so on. In addition, the image capturing section 104 may include an RGB color filter and the like, and the image capturing element may capture an image of light having been transmitted through the color filter.

The control circuit 105 controls the irradiating section 101, the variable spectroscopic element 103, the image capturing section 104, and the communicating section 106. The control circuit 105 controls the variable spectroscopic element 103 to vary the light of the wavelength to be transmitted. As a result, the image capturing section 104 can capture images of light rays of different wavelengths. The control circuit 105 generates a multi-band image indicating the intensity of light rays of a plurality of wavelengths, from the plurality of wavelength images captured by the image capturing section 104. The communicating section 106 transmits the generated multi-band image to the computer 200 such as a personal computer.

As a result, an operator of the computer 200 can designate the disease condition to be observed, by analyzing the received multi-band image. The computer 200 may also analyze the received multi-band image, to designate the disease condition to be observed. The term "disease condition" used here includes a type of the disease of the examinee, and the degree of progress of the disease of the examinee. In this case, the computer 200 transmits information indicating the designated disease condition to the image capturing apparatus 100. The image capturing apparatus 100 identifies the disease condition indicated by the received information as the observation target. Alternatively, the image capturing apparatus 100 may identify the disease condition to be observed by analyzing the multi-band image.

Once the disease condition is identified, the control circuit 105 controls the variable spectroscopic element to sequentially transmit light rays of a plurality of wavelengths within the range of the wavelength band according to the identified disease condition. The image capturing section 104 sequentially captures the image of the light of the wavelength sequentially transmitted through the variable spectroscopic element. This enables the light of the wavelength necessary for diagnosing the disease condition to be observed, and helps reduce the amount of information. Specifically, if the light rays of a plurality of wavelengths included in the wide wavelength band are sequentially captured, the amount of information gets large, and results in capturing light of a wavelength that is not necessary for diagnosis of the disease condition to be observed, which is a waste. Only the light rays of a plurality of wavelengths within the range of the wavelength band corresponding to a particular disease condition may be designed to be mainly transmitted. The control circuit 105 generates a multi-band image using images of light rays of respective wavelengths within the wavelength band corresponding to the disease condition captured by the image capturing section 104. The communicating section 106 transmits the generated multi-band image to the computer 200. Accordingly, the multi-band image of the wavelength band corresponding to the disease condition can be transmitted, which helps reduce the amount of information, and reduce unnecessary information.

Figure 2:
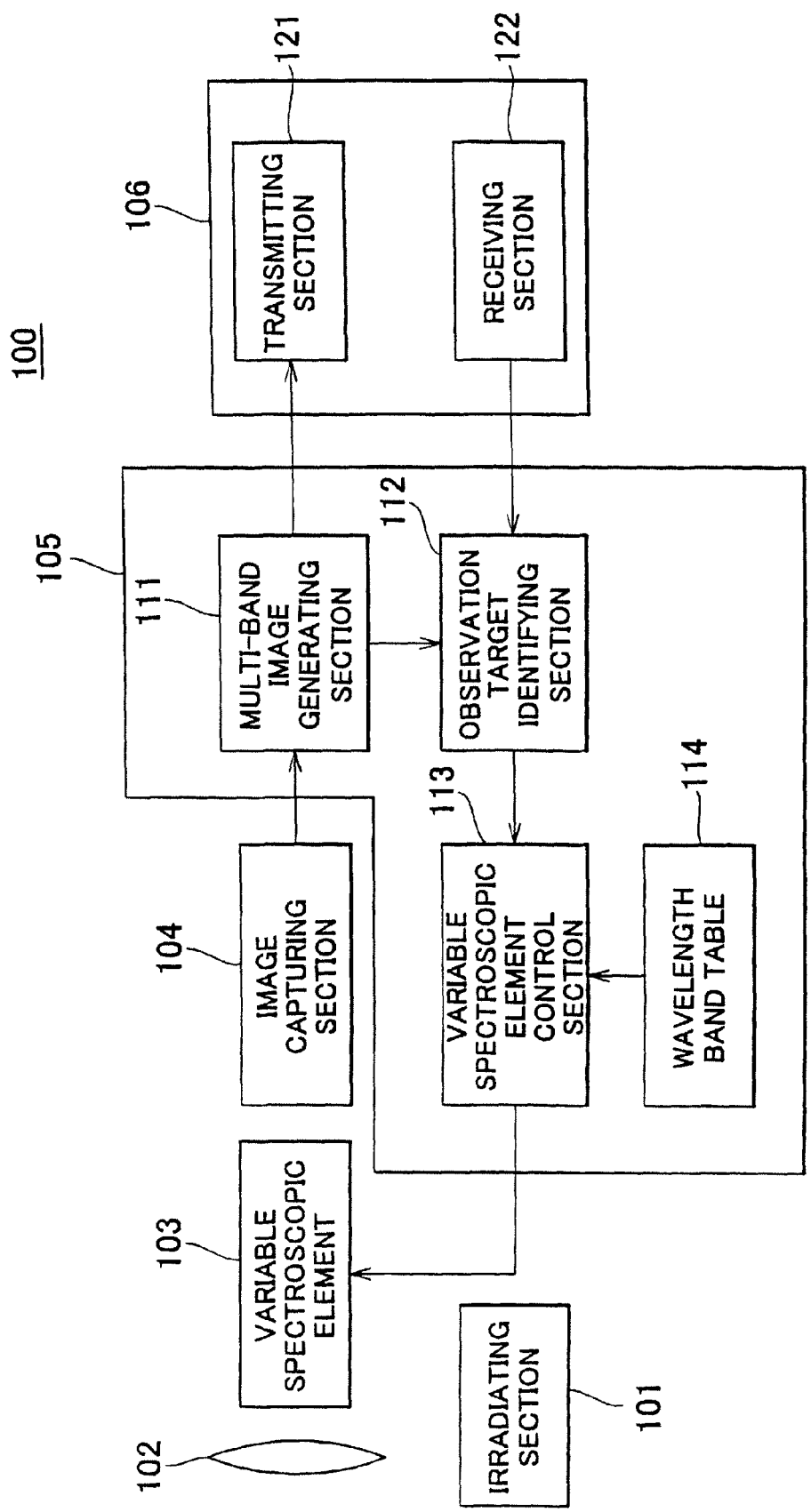
FIG. 2 shows a detailed view of an image capturing apparatus 100.

FIG. 2 shows a detailed view of an image capturing apparatus 100. In FIG. 2, the same reference numerals are assigned to the same elements in FIG. 1. The control circuit 105 includes a multi-band image generating section 111, an observation target identifying section 112, a variable spectroscopic element control section 113, and a wavelength band table 114. The communicating section 106 includes a transmitting section 121 and a receiving section 122. The control circuit 105 may be realized by electronic circuitry or electric circuitry, or by an information processing apparatus such as a CPU. In addition, the communicating section 106 may be realized by a CCU (communication control unit), or by Bluetooth (registered trademark) or the like.

The multi-band image generating section 111 generates a multi-band image, using the images of the light rays of a plurality of wavelengths sequentially captured by the image capturing section 104. The multi-band image shows the intensity of the light rays of a plurality of wavelengths sequentially captured by the image capturing section 104, for each of the plurality of pixels. The multi-band image generating section 111 outputs the generated multi-band image to the observation target identifying section 112 and the transmitting section 121. The transmitting section 121 outputs the multi-band image to the computer 200. The receiving section 122 receives information indicating the disease condition transmitted from the computer.

The observation target identifying section 112 identifies the disease condition to be observed. The observation target identifying section 112 may identify the disease condition to be observed, from the multi-band image generated by the multi-band image generating section 111. A normal living tissue has such a characteristic that the intensity of the light of a certain wavelength is high, and the intensity of the light of another wavelength is low. Whereas in the case of a living tissue suffering from a disease condition, the intensity of the light of the wavelength that is high for a normal living tissue is low, and the intensity of the light of the wavelength that is low for a normal living tissue is high. Therefore, by analyzing the multi-band image, it is possible to identify the suspect disease condition as a disease condition to be observed. The observation target identifying section 112 may include data of the wavelength characteristics for each disease condition that is different from the normal case, so that the observation target identifying section 112 can identify the disease condition to be observed, using the data. When the receiving section 122 has received information indicating a disease condition, the observation target identifying section 112 may identify the disease condition indicated by the information received by the receiving section 122, to be the disease condition to be observed.

The variable spectroscopic element control section 113 controls the wavelength of light transmitted through the variable spectroscopic element 103. When the observation target identifying section 112 has identified a disease condition, the variable spectroscopic element control section 113 controls the variable spectroscopic element 103 to sequentially transmit the light rays of a plurality of wavelengths within the range of the wavelength band corresponding to the identified disease condition. The wavelength band table 114 records therein wavelength bands corresponded with disease conditions. The variable spectroscopic element control section 113 reads, from the wavelength band table 114, the wavelength band corresponding to the disease condition identified by the observation target identifying section 112, to control the variable spectroscopic element 103. The variable spectroscopic element control section 113 also controls the wavelength interval of the wavelength of the light that is transmitted through the variable spectroscopic element.

Figure 3:
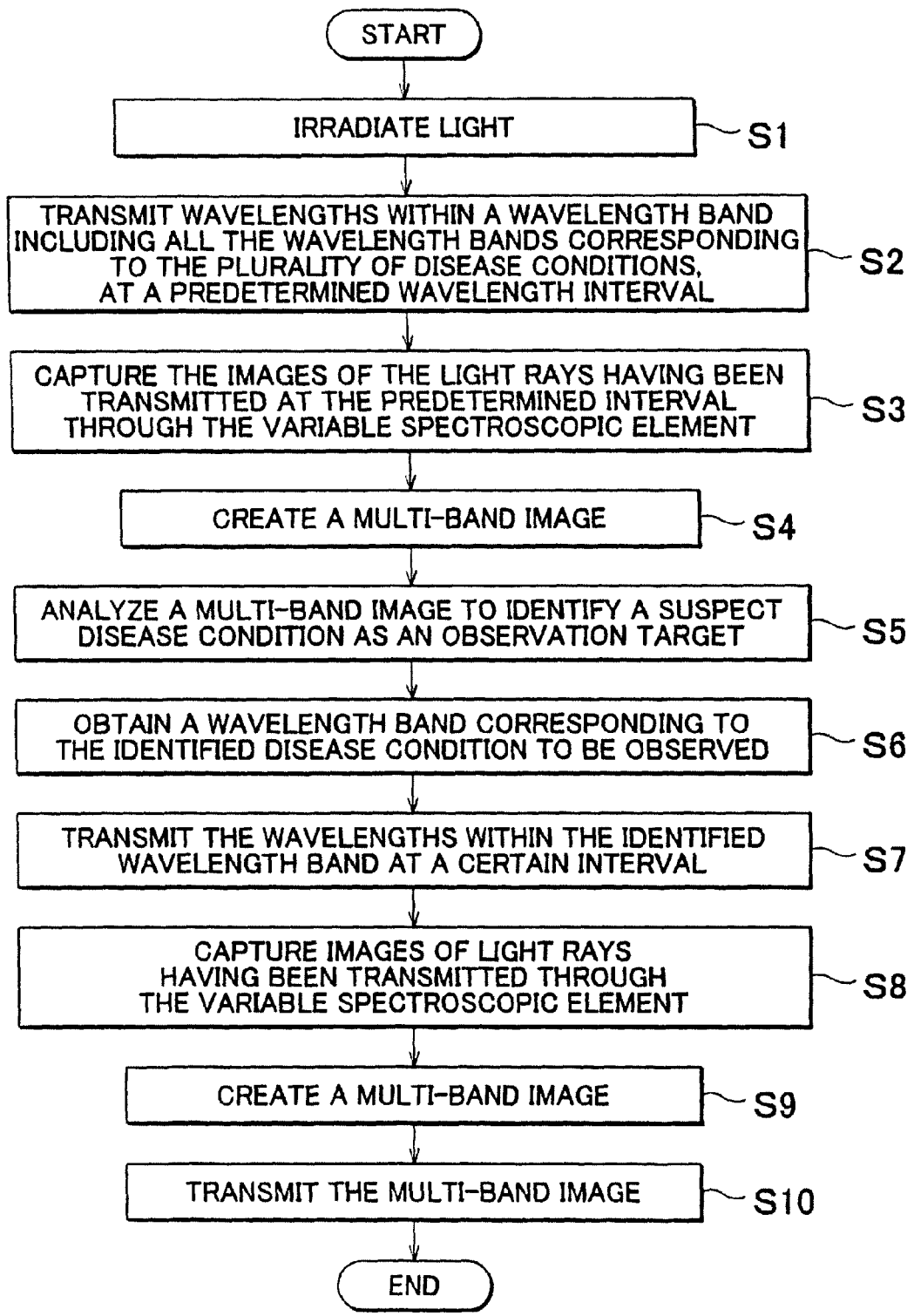
FIG. 3 shows an example of the flowchart of the operation of the image capturing apparatus 100.

FIG. 3 shows an example of the flowchart of the operation of the image capturing apparatus 100. At Step S1, the irradiating section 101 irradiates a subject, being a living tissue, with light. The irradiating section 101 may irradiate white light, or irradiate light of a predetermined wavelength band. In addition, the irradiating section 101 may irradiate excitation light. The irradiating section 101 may irradiate a plurality of rays of excitation light. Here, excitation light is used to excite a plurality of wavelength fluorescent light rays. At Step S2, the variable spectroscopic element control section 113 controls the variable spectroscopic element 103 to transmit the light rays of wavelengths within the wavelength band range including all the wavelength bands respectively corresponding to the plurality of disease conditions recorded in the wavelength band table 114, at a predetermined wavelength interval. At Step S3, the image capturing section 104 sequentially captures the images of the light rays having been transmitted at the predetermined interval through the variable spectroscopic element 103. Specifically, the image capturing section 104 captures the image of the light of the certain wavelength having been transmitted through the variable spectroscopic element 103, and outputs the image to the multi-band image generating section 111. Thereafter, the image of the light of a different wavelength subsequently transmitted through the variable spectroscopic element 103 is captured, and outputted to the multi-band image generating section 111. In this way, images of light of wavelengths transmitted through the variable spectroscopic element 103 are captured, and the images are outputted to the multi-band image generating section 111.

Figure 4A:
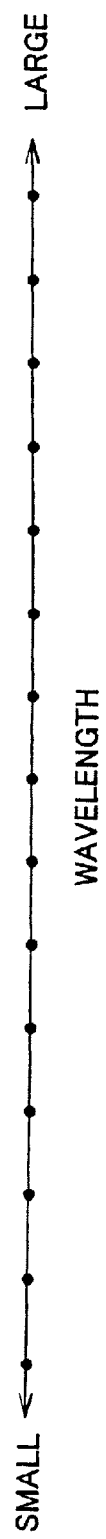
FIG. 4A, FIG. 4B, and FIG. 4C show an example of the wavelength of light transmitted through a variable spectroscopic element 103.
Figure 4B:
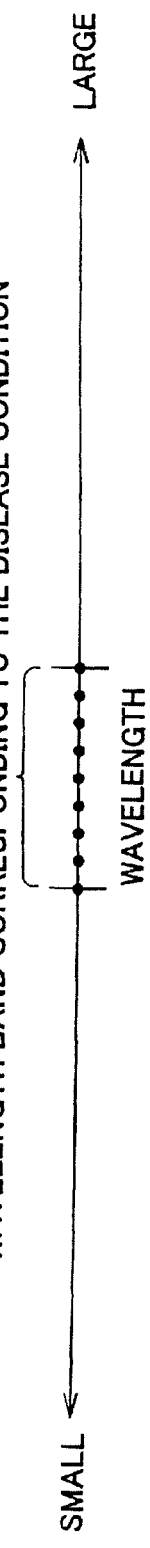
Figure 4C:
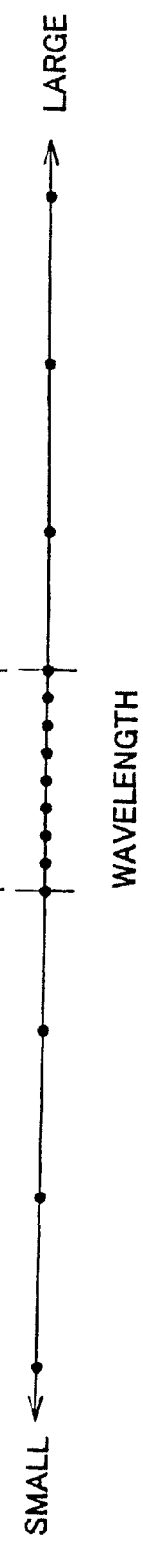

FIG. 4A, FIG. 4B, and FIG. 4C show an example of the wavelength of light transmitted through the variable spectroscopic element 103. The lateral axis indicates a wavelength. The wavelength gets large towards the right, and gets small towards the left. The black dot indicates the wavelength of light transmitted through the variable spectroscopic element 103. FIG. 4A shows an example of the light wavelength within the wavelength band range, which includes the wavelength bands corresponding to the plurality of disease conditions transmitted through the variable spectroscopic element 103. The variable spectroscopic element 103 sequentially transmits the light at a predetermined wavelength interval. The image capturing section 104 sequentially captures the images of the light rays of respective wavelengths sequentially transmitted through the variable spectroscopic element 103, and outputs the images to the multi-band image generating section 111.

Here, referring back to the flowchart of FIG. 3, at Step S4, the multi-band image generating section 111 uses the respective wavelength images captured by the image capturing section 104 to generate a multi-band image showing the intensity of light rays of a plurality of wavelengths sequentially captured by the image capturing section 104, for each of a plurality of pixels included in the image capturing section 104. The generated multi-band image indicates the intensity of the light rays of a plurality of wavelengths captured by the pixels of the image capturing section 104. Note that the multi-band image generating section 111 may generate a multi-band image showing the intensity of the light rays of a plurality of wavelengths for each block, where one block has m pixels*n pixels. Here, "m" and "n" are natural numbers. A multi-band image may also be generated in which all the pixels of the image capturing section 104 are set as one block.

Figure 5:
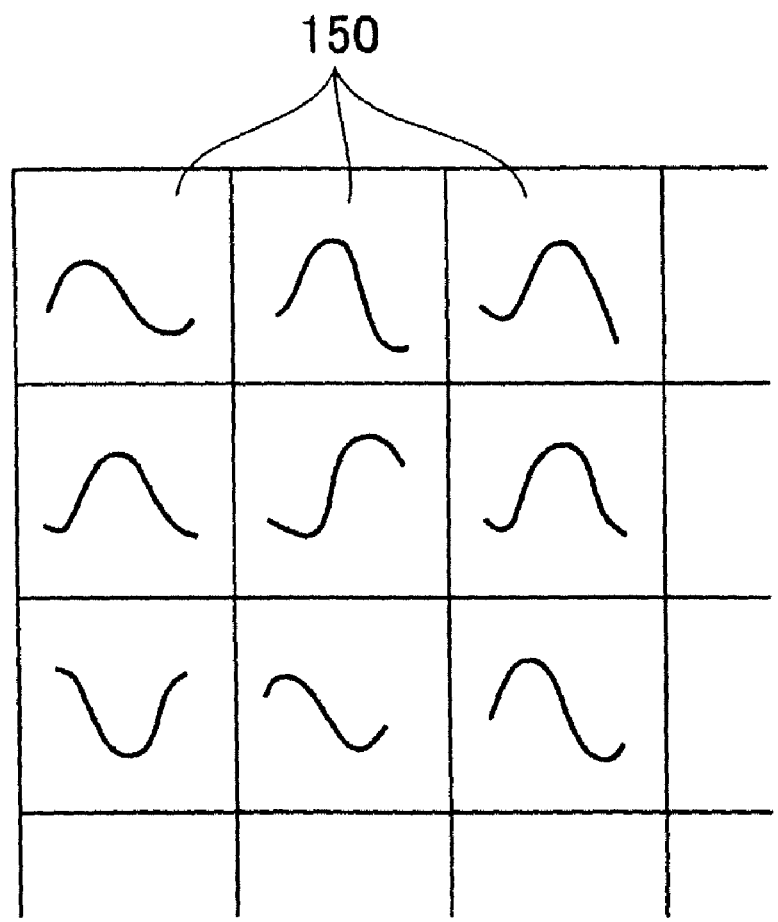
FIG. 5 shows a concept of a multi-band image generated to show the intensity of captured light rays of a plurality of wavelengths, for each of a plurality of pixels.

FIG. 5 shows a schematic view of a multi-band image generated to show the intensity of the captured light rays of a plurality of wavelengths, for each of a plurality of pixels. The multi-band image shows the intensity of the light rays of a plurality of wavelengths for each pixel 150 of the image capturing section 104. For the wavelength spectrum shown in each pixel 150, the lateral axis indicates the wavelength, and the longitudinal axis indicates the optical intensity.

Now, referring back to the flowchart of FIG. 3, at Step S5, the observation target identifying section 112 analyzes the multi-band image generated by the multi-band image generating section 111, and identifies the suspect disease condition as the disease condition to be observed. Alternatively, the computer 200 may analyze the multi-band image, to identify a suspect disease condition. In this case, the transmitting section 121 transmits the multi-band image to the computer 200, so that the computer 200 may analyze the multi-band image, to identify a suspect disease condition. A doctor may analyze the multi-band image received by the computer 200, and input a suspect disease condition. The computer 200 transmits information indicating the suspect disease condition to the image capturing apparatus 100. The receiving section 122 receives the information indicating the disease condition transmitted from the computer 200, and outputs it to the observation target identifying section 112. The observation target identifying section 112 identifies the disease condition indicated by the information received by the receiving section 122 as the disease condition to be observed.

At Step S6, the variable spectroscopic element control section 113 obtains, from the wavelength band table 114, the wavelength band corresponding to the disease condition identified by the observation target identifying section 112. At Step S7, the variable spectroscopic element control section 113 controls the variable spectroscopic element 103 to sequentially transmit the light rays of a plurality of wavelengths within the range of the wavelength band corresponding to the disease condition identified by the observation target identifying section 112. The variable spectroscopic element control section 113 may sequentially transmit the light rays of a plurality of wavelengths within the range of the wavelength band corresponding to the identified disease condition, at a certain wavelength interval. This certain wavelength interval is shorter than the predetermined wavelength interval. Accordingly, so as to identify the disease condition, the suspect disease condition is first identified by coarsely sampling the wavelength light in a wide range. Once the disease condition is identified, finer sampling is performed to the wavelength light in the wavelength band corresponding to the identified disease condition, thereby improving the diagnosis accuracy of the identified disease condition. This method also helps reduce the information amount of data. Note that the variable spectroscopic element control section 113 may vary the wavelength interval of the light transmitted within the range of the wavelength band, according to the width of the wavelength band corresponding to the disease condition identified by the observation target identifying section 112.

FIG. 4B and FIG. 4C respectively show an example of the wavelength of light within the range of the wavelength band corresponding to the identified disease condition transmitted through the variable spectroscopic element 103. FIG. 4B shows an example of transmitting only the light of the wavelength band corresponding to the identified disease condition. The wavelength interval between the light rays of a plurality of wavelengths within the wavelength band corresponding to the identified disease condition transmitted through the variable spectroscopic element 103 is shorter than the wavelength interval of FIG. 4A. As a result, the data amount can be reduced compared to the case of transmitting the light of the wavelength within the wavelength band range including the wavelength bands respectively corresponding to the plurality of disease conditions. Moreover, the diagnosis accuracy of the identified disease condition improves, because the light rays of a plurality of wavelengths within the range of the wavelength band corresponding to the identified disease condition are transmitted at a wavelength interval shorter than the predetermined wavelength interval. Note that the variable spectroscopic element control section 113 may vary the wavelength interval of the light transmitted within the wavelength band range, according to the width of the wavelength band corresponding to the disease condition identified by the observation target identifying section 112. That is, the certain wavelength interval may be changed according to the width of the wavelength band corresponding to the identified disease condition. For example, when the wavelength band corresponding to the identified disease condition is narrow, the certain wavelength interval may be shortened compared to the example where the wavelength band corresponding to the identified disease condition is wide.

FIG. 4C shows an example of mainly transmitting the light of the wavelength within the range of the wavelength band corresponding to the identified disease condition. The wavelength interval between the light rays of a plurality of wavelengths within the range of the wavelength band corresponding to the identified disease condition, which is transmitted through the variable spectroscopic element 103, is shorter than the wavelength interval between the light rays of a plurality of wavelengths outside the wavelength band corresponding to the identified disease condition. In addition, the wavelength interval between the light rays of a plurality of wavelengths within the range of the wavelength band corresponding to the identified disease condition, which is transmitted through the variable spectroscopic element 103, is shorter than the predetermined wavelength interval of FIG. 4A. Moreover, the wavelength interval between the light rays of a plurality of wavelengths within a wavelength band outside the wavelength band corresponding to the identified disease condition, which is transmitted through the variable spectroscopic element 103, is longer than the predetermined wavelength interval of FIG. 4A. As a result, the data amount can be reduced compared to the case of transmitting the light of the wavelength within the wavelength band range including the wavelength bands respectively corresponding to the plurality of disease conditions. Moreover, the diagnosis accuracy of the identified disease condition improves, because the light rays of a plurality of wavelengths within the range of the wavelength band corresponding to the identified disease condition are transmitted at a wavelength interval shorter than the predetermined wavelength interval. Furthermore, another disease condition not identified can also be diagnosed, because the light of a wavelength within a wavelength band outside the wavelength band corresponding to the identified disease condition. Note that the variable spectroscopic element control section 113 may vary the wavelength interval of the light transmitted within the wavelength band range, according to the width of the wavelength band corresponding to the disease condition identified by the observation target identifying section 112. That is, the certain wavelength interval may be changed according to the width of the wavelength band corresponding to the identified disease condition. For example, when the wavelength band corresponding to the identified disease condition is narrow, the certain wavelength interval may be shortened compared to the example where the wavelength band corresponding to the identified disease condition is wide.

Here, referring back to the flowchart of FIG. 3, at Step S8, the image capturing section 104 sequentially captures the images of the light rays of a plurality of wavelengths having been transmitted through the variable spectroscopic element 103. At Step S9, the multi-band image generating section 111 uses the respective wavelength images captured by the image capturing section 104 to generate a multi-band image showing the intensity of light rays of a plurality of wavelengths sequentially captured by the image capturing section 104, for each of a plurality of pixels included in the image capturing section 104. At Step S10, the transmitting section 121 transmits the multi-band image generated by the multi-band image generating section 111 to the computer 200.

Figure 6:
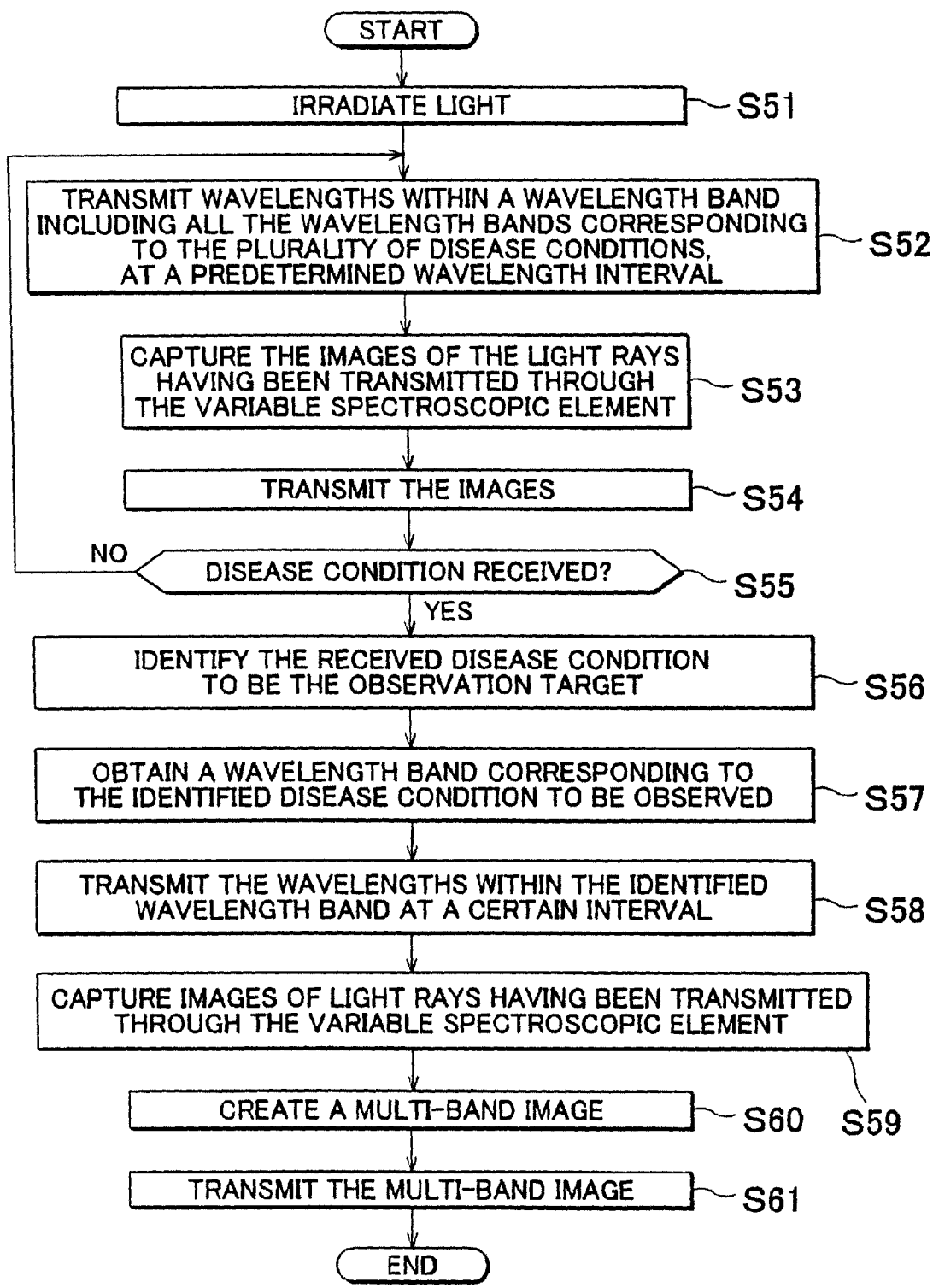
FIG. 6 shows another example of the flowchart of the operation of the image capturing apparatus 100.

FIG. 6 shows another example of the flowchart of the operation of the image capturing apparatus 100. At Step S51, the irradiating section 101 irradiates a subject, being a living tissue, with light. The irradiating section 101 may irradiate white light, and light of a predetermined wavelength band. The irradiating section 101 may irradiate excitation light. At Step S52, the variable spectroscopic element control section 113 controls the variable spectroscopic element 103 to transmit the light rays of a plurality of wavelengths within the wavelength band range including the wavelength bands respectively corresponding to the plurality of disease conditions recorded in the wavelength band table 114, at a predetermined wavelength interval. At Step S53, the image capturing section 104 captures the images of light rays including a plurality of wavelengths having been transmitted through the variable spectroscopic element 103. The image capturing section 104 captures the images of the light rays of a plurality of wavelengths having been transmitted through the variable spectroscopic element 103, in a single exposure. That is, the variable spectroscopic element control section 113 controls the variable spectroscopic element 103 to transmit the light rays of a plurality of wavelengths within the wavelength band range including the wavelength bands respectively corresponding to the plurality of disease conditions, in a single exposure of the image capturing section 104. Accordingly, the image capturing section 104 can obtain images of the light rays of a plurality of wavelengths.

At Step S54, the transmitting section 121 transmits the images captured by the image capturing section 104, to the computer 200. That is, the images are sent to the transmitting section 121, and the multi-band image generating section 111 does not generate any multi-band image using the images captured by the image capturing section 104. The transmitting section 121 outputs the images captured by the image capturing section 104. At Step S55, the observation target identifying section 112 determines whether information indicating a disease condition is transmitted from the receiving section 122. When the determination results in the negative at Step S55, the control returns to Step S52, to repeat the aforementioned operations. Accordingly, until the computer 200 transmits information indicating a disease condition to the image capturing apparatus 100, the computer 200 can sequentially display the images captured by the image capturing apparatus 100. A user such as a doctor can input a suspect disease condition to the computer 200, by observing the displayed images. When a disease condition is inputted, the computer 200 transmits information indicating the inputted disease condition to the image capturing apparatus 100. The receiving section 122 outputs the disease condition indicated by the received information, to the observation target identifying section 112.

When the determination results in the affirmative in Step S55, the observation target identifying section 112 determines the disease condition indicated by the received information, as an observation target in Step S56. At Step S57, the variable spectroscopic element control section 113 obtains, from the wavelength band table 114, the wavelength band corresponding to the disease condition identified by the observation target identifying section 112. At Step S58, the variable spectroscopic element control section 113 controls the variable spectroscopic element to sequentially transmit the light rays of a plurality of wavelengths within the range of the wavelength band corresponding to the disease condition identified by the observation target identifying section 112. At Step S59, the image capturing section 104 sequentially captures the images of the light rays of a plurality of wavelengths having been transmitted through the variable spectroscopic element 103. That is, the image capturing section 104 sequentially captures the images of the light rays of respective wavelengths having been transmitted through the variable spectroscopic element 103. At Step S60, the multi-band image generating section 111 uses the respective wavelength images captured by the image capturing section 104 to generate a multi-band image showing the intensity of light rays of a plurality of wavelengths sequentially captured by the image capturing section 104, for each of a plurality of pixels included in the image capturing section 104. At Step S61, the transmitting section 121 transmits the multi-band image generated by the multi-band image generating section 111, to the computer 200. The operations from Step S57 through Step S61 may be the same as the operations from Step S6 through Step S10 of FIG. 3.

Note that at Step S52, the variable spectroscopic element 103 may retreat from the optical path. In this case, at step S53, the image capturing section 104 captures the images of the light transmitted through the lens 102 as it is. In this case, after finishing the operation of Step S55 and before starting the operation of Step S58, the variable spectroscopic element 103 is returned on the optical path. At Step S53, the image capturing section 104 captures the images of the light rays of a plurality of wavelengths having been transmitted through the variable spectroscopic element 103, in a single exposure. Alternatively, however, the light rays of respective wavelengths transmitted through the variable spectroscopic element 103 may be sequentially captured, i.e. the image capturing section 104 may perform the same operation as in Step S3 of FIG. 3. In doing so, the multi-band image generating section 111 may combine images of respective wavelengths, to generate a single image including light rays of a plurality of wavelengths. The generated image is transmitted to the computer 200 from the transmitting section 121.

In this way, the variable spectroscopic element 103 is controlled to transmit the light rays of a plurality of wavelengths within the range of the wavelength band corresponding to the suspect disease condition to sequentially capture the images of the wavelengths light rays, which helps reduce the amount of data, and improve the diagnosis accuracy of the identified disease condition. In addition, the light of the wavelength band corresponding to the identified disease condition is mainly transmitted, which also helps improve the diagnosis accuracy of the identified disease condition, and reduce the amount of data. That is, since only the wavelength light within the range of the wavelength band corresponding to the identified disease condition is allowed to be transmitted, the wavelength interval of the transmitted light can be shortened, to improve the diagnosis accuracy of the disease condition. The diagnosis accuracy of a disease condition improves because the light of a wavelength within the range of the wavelength band corresponding to the identified disease condition is transmitted at a short wavelength interval, and the light of a wavelength within a wavelength band outside the wavelength band corresponding to the identified disease condition is transmitted at a long wavelength interval. Note that the image capturing apparatus 100 is not limited to the encapsulated endoscope explained in the above-described embodiment, and may be applied to an endoscope apparatus, a camera, and so on. Furthermore, an information processing apparatus such as a CPU may function as the image capturing apparatus 100, by executing a predetermined program.

In the above-described embodiment, when the base spectrum of the living tissue is already known, the data may be transmitted in a reduced amount as detailed below. The multi-band image obtained by sequentially capturing the images of light of wavelengths within the wavelength band range including the wavelength bands respectively corresponding to a plurality of disease conditions may correspond to a summation of values of the base spectra. For example, when there are only a base spectrum of collagen, a base spectrum of medicine, and a base spectrum of NADH, the wavelength spectra respectively of the pixels of the resulting multi-band image will be a summation of values of the base spectra multiplied by respective weighting coefficients. Therefore, the control circuit 105 calculates the weighting coefficients for the base spectra for each of the pixels, so that the wavelength spectrum resulting from summing the base spectra multiplied by the weighting coefficients corresponds to the multi-band image. The transmitting section 121 may transmit, to the computer 200, the calculated weighting coefficients for the respective base spectra for each pixel. In this way, the computer 200 can generate a multi-band image using the known base spectra and the weighting coefficients.

When the base spectra are unknown, the control circuit 105 may analyze the principal components of the multi-band image, to obtain the principal components having a spectrum change larger than a predetermined value. Then weighting coefficients of the principal components are calculated for each pixel. The transmitting section 121 transmits, to the computer 200, the calculated principal components and the weight coefficients for the respective pixels. In this way, the computer 200 can generate a multi-band image using the principal components and the weighting coefficients for the respective pixels.

Although some aspects of the present invention have been described by way of exemplary embodiments, it should be understood that those skilled in the art might make many changes and substitutions without departing from the spirit and the scope of the present invention which is defined only by the appended claims.

The operations, the processes, the steps, or the like in the apparatus, the system, the program, and the method described in the claims, the specification, and the drawings are not necessarily performed in the described order. The operations, the processes, the steps, or the like can be performed in an arbitrary order, unless the output of the former-described processing is used in the later processing. Even when expressions such as "First," or "Next," or the like are used to explain the operational flow in the claims, the specification, or the drawings, they are intended to facilitate the understanding of the invention, and are never intended to show that the described order is mandatory.

What is claimed is:

1. An image capturing apparatus, comprising:
   an irradiating section that emits a light to a subject;
   a variable spectroscopic element capable of varying a wavelength of a light from the subject to be transmitted;
   a wavelength band table recording therein wavelength bands corresponded with disease conditions;
   an observation target identifying section that identifies a disease condition to be observed;
   a variable spectroscopic element control section that controls the variable spectroscopic element to sequentially transmit light rays of a plurality of wavelengths including all wavelength bands corresponding to a plurality of disease conditions recorded in the wavelength band table;
   an image capturing section that sequentially captures images by the light rays of the plurality of wavelengths transmitted through the variable spectroscopic element; and
   a multi-band image generating section that uses respective wavelength images captured by the image capturing section to generate a multi-band image,
   wherein the observation target identifying section analyzes the multi-band image to identify the disease condition to be observed.

2. The image capturing apparatus according to claim 1, wherein the variable spectroscopic element control section controls the variable spectroscopic element to transmit light of a wavelength within a range of a wavelength band corresponding to the disease condition identified by the observation target identifying section, at a wavelength interval shorter than a wavelength interval of light of a wavelength outside the wavelength band corresponding to the identified disease condition.

3. The image capturing apparatus according to claim 2, wherein according to a width of the wavelength band corresponding to the disease condition identified by the observation target identifying section, the variable spectroscopic element control section varies a wavelength interval of light transmitted within the range of the wavelength band corresponding to the identified disease condition.

4. The image capturing apparatus according to claim 1, wherein the variable spectroscopic element control section controls the variable spectroscopic element to transmit, at a predetermined wavelength interval, a light of a wavelength within a wavelength band range including the wavelength bands respectively corresponding to the disease conditions recorded in the wavelength band table, and
   wherein, when the observation target identifying section has identified the disease condition, the variable spectroscopic element control section controls the variable spectroscopic element to transmit a light of a wavelength band corresponding to the identified disease condition, at a wavelength interval shorter than the predetermined wavelength interval.

5. The image capturing apparatus according to claim 1, the multi-band image indicating, for each of a plurality of pixels, an intensity of the light rays of a plurality of wavelengths sequentially captured by the image capturing section.

6. An endoscope apparatus comprising the image capturing apparatus according to claim 1.

7. An encapsulated endoscope comprising the image capturing apparatus according to claim 1.

8. The encapsulated endoscope according to claim 7, further comprising:
   a transmitting section that transmits, to an outside of the image capturing apparatus, the images captured by the image capturing section.

9. The image capturing apparatus according to claim 8, further comprising:
   a receiving section that receives, from an outside of the image capturing apparatus, information indicating the disease condition to be observed,
   wherein the observation target identifying section, upon reception of the information by the receiving section from outside, identifies the disease condition indicated by the information to be the disease condition to be observed,
   wherein, when the receiving section has not received the information from said outside, the transmitting section transmits, to said outside, the images sequentially captured by the image capturing section by light rays of a plurality of wavelengths within the wavelength band range including the wavelength bands respectively corresponding to the disease conditions, and
   wherein, when the receiving section has received the information from said outside, the transmitting section transmits, to said outside, the images sequentially captured by the image capturing section by the light rays of a plurality of wavelengths within the range of the wavelength band corresponding to the disease condition identified by the observation target identifying section.

10. An image capturing method, comprising:
    identifying a disease condition to be observed;
    emitting a light to a subject;

obtaining a wavelength band corresponding to the identified disease condition, from a wavelength band table recording therein wavelength bands corresponded with disease conditions;

sequentially transmitting light rays of a plurality of wavelengths including all wavelength bands corresponding to a plurality of disease conditions at predetermined intervals recorded in the wavelength band table, by controlling a variable spectroscopic element capable of varying a wavelength of a light of the subject to be transmitted;

sequentially capturing images by the light rays of the plurality of wavelengths transmitted through the variable spectroscopic element; and generating a multi-band image by using respective wavelength images captured by the sequentially capturing images, wherein the identifying the disease condition comprise analyzing the multi-band image to identify the disease condition to be observed.

11. The image capturing method according to claim 10, wherein the controlling the variable spectroscopic element includes:

controlling transmitting a light of a wavelength within a range of the wavelength band corresponding to the identified disease condition, at a wavelength interval shorter than a wavelength interval of light of a wavelength outside the wavelength band corresponding to the identified disease condition.

12. The image capturing method according to claim 11, wherein the controlling the variable spectroscopic element includes:

according to a width of the wavelength band corresponding to the identified disease condition, varying a wavelength interval of light transmitted within the range of the wavelength band corresponding to the identified disease condition.

13. The image capturing method according to claim 10, wherein the controlling the variable spectroscopic element includes:

controlling transmitting, at a predetermined wavelength interval, a light of a wavelength within a wavelength band range including the wavelength bands respectively corresponding to the disease conditions recorded in the wavelength band table, and, when the disease condition has been identified, controlling the variable spectroscopic element to transmit light of a wavelength band corresponding to the identified disease condition, at a wavelength interval shorter than the predetermined wavelength interval.

14. The image capturing method according to claim 10, wherein the multi-band image indicates, for each of a plurality of pixels, an intensity of the sequentially captured light rays of a plurality of wavelengths.

15. A non-transitory computer readable medium storing therein a program in a computer, including a wavelength band table recording therein wavelength bands corresponded with disease conditions, the program causing the computer to function as:

an irradiating section for controlling an emission of a light to a subject;

an observation target identifying section that identifies a disease condition to be observed;

a variable spectroscopic element control section that controls a variable spectroscopic element to sequentially transmit light rays of a plurality of wavelengths including all wavelength bands corresponding to a plurality of disease conditions at predetermined intervals recorded in the wavelength band table, the variable spectroscopic element being capable of varying a wavelength of a light of the subject to be transmitted;

an image capturing section that sequentially captures images by the light rays of the plurality of wavelengths transmitted through the variable spectroscopic element; and a multi-band image generating section that uses respective wavelength images captured by the image capturing section to generate a multi-band image, wherein the observation target identifying section analyzes the multi-band image to identify the disease condition to be observed.

16. The non-transitory computer readable medium according to claim 15, wherein the variable spectroscopic element control section controls the variable spectroscopic element to transmit a light of a wavelength within a range of a wavelength band corresponding to the disease condition identified by the observation target identifying section, at a wavelength interval shorter than a wavelength interval of light of a wavelength outside the wavelength band corresponding to the identified disease condition.

17. The non-transitory computer readable medium according to claim 16, wherein according to a width of the wavelength band corresponding to the disease condition identified by the observation target identifying section, the variable spectroscopic element control section varies a wavelength interval of light transmitted within the range of the wavelength band corresponding to the identified disease condition.

18. The non-transitory computer readable medium according to claim 15, wherein the variable spectroscopic element control section controls the variable spectroscopic element to transmit, at a predetermined wavelength interval, a light of a wavelength within a wavelength band range including the wavelength bands respectively corresponding to the disease conditions recorded in the wavelength band table, and wherein, when the observation target identifying section has identified the disease condition, the variable spectroscopic element control section controls the variable spectroscopic element to transmit light of a wavelength band corresponding to the identified disease condition, at a wavelength interval shorter than the predetermined wavelength interval.

19. The non-transitory computer readable medium according to claim 15, the multi-band image indicating, for each of a plurality of pixels, an intensity of the light rays of a plurality of wavelengths sequentially captured by the image capturing section.

* * * * *